United States Patent [19]

Ishida et al.

[11] Patent Number: 5,002,556
[45] Date of Patent: Mar. 26, 1991

[54] BALLOON CATHETER ASSEMBLY

[75] Inventors: Toshinobu Ishida; Susumu Tanabe, both of Fuji, Japan

[73] Assignee: Terumo Kabushiki Kaisha, Tokyo, Japan

[21] Appl. No.: 363,889
[22] PCT Filed: Nov. 27, 1987
[86] PCT No.: PCT/JP87/00922
 § 371 Date: May 24, 1989
 § 102(e) Date: May 24, 1989
[87] PCT Pub. No.: WO88/03817
 PCT Pub. Date: Jun. 2, 1988

[30] Foreign Application Priority Data

Nov. 29, 1986 [JP] Japan .................. 61-284606
Nov. 29, 1986 [JP] Japan .................. 61-284607
Nov. 29, 1986 [JP] Japan .................. 61-284608

[51] Int. Cl.$^5$ ............................ A61M 29/02
[52] U.S. Cl. ............................ 606/191; 606/192; 604/96
[58] Field of Search ............ 604/96, 97, 98, 102, 604/103, 104; 606/191, 192, 194, 195

[56] References Cited

U.S. PATENT DOCUMENTS 4,402,319 9/1983 Handa et al. ............... 604/103 X
4,520,823 6/1985 LeVeen et al. ................ 606/195
4,545,367 10/1985 Tucci .
4,802,479 2/1989 Haber et al. ................. 606/192

FOREIGN PATENT DOCUMENTS 056103 7/1982 European Pat. Off. .
3222795 12/1983 Fed. Rep. of Germany .
2361124 3/1978 France .
54-54487 4/1979 Japan .
88/04560 6/1988 World Int. Prop. O. ............ 604/96

Primary Examiner—Robert A. Hafer
Assistant Examiner—Kerry Owens
Attorney, Agent, or Firm—Frishauf, Holtz, Goodman & Woodward

[57] ABSTRACT

A balloon catheter assembly including a balloon and a catheter. The catheter has a chuck and a multi-tube unit including at least an inner tube and an outer tube arranged slidably and coaxially with the inner tube. The balloon is removably fixed to the distal portion of the inner tube by the chuck which is pulled into the outer tube to be closed, and which is extended from the outer tube to be opened. The catheter is introduced to a required dwelling portion in a blood vessel by a tubular guide sheath having an inner diameter such that the guide sheath admits the catheter, and the expanded balloon is left in the dwelling portion to occlude the blood vessel.

30 Claims, 5 Drawing Sheets

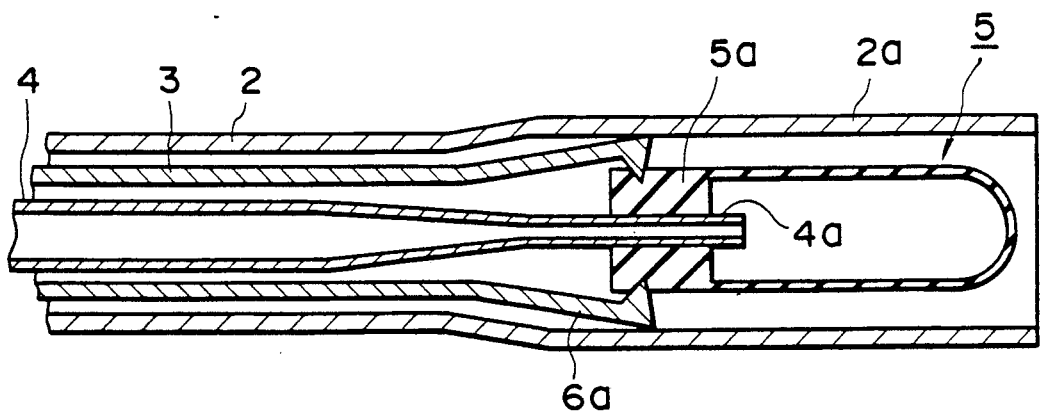
F I G. 6
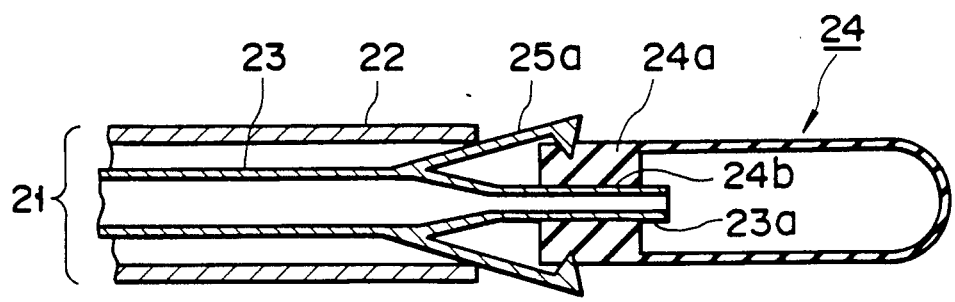
F I G. 7
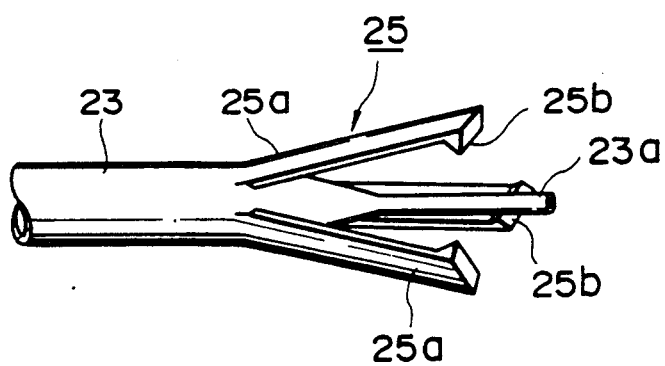
F I G. 8

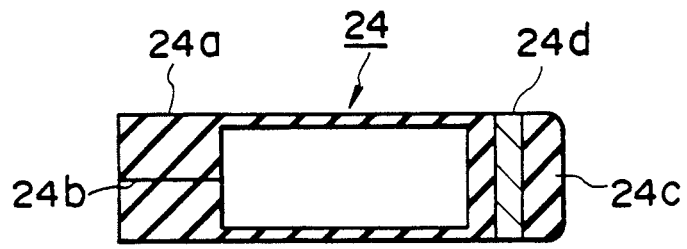
F I G. 11
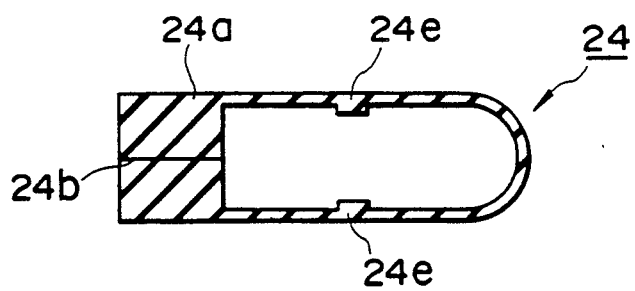
F I G. 12
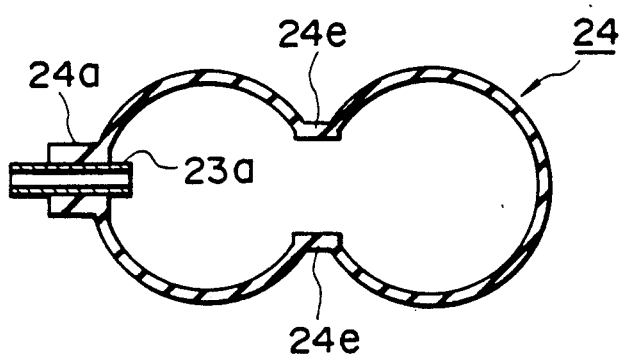
F I G. 13

BALLOON CATHETER ASSEMBLY

BACKGROUND OF THE INVENTION

This invention relates to a balloon catheter assembly comprising a detachable occluding balloon for occluding a path of a body fluid such as a blood vessel, and to a guide sheath for guiding the introduction of the catheter.

An occluding balloon is used for mainly occluding a blood vessel such as an artery when, for example, a percutaneous surgery of congenital cardiopathy due to patent duct arteriosus is carried out.

The PCT Patent Publication Sho 57-500720, for example, discloses a balloon catheter having an occluding balloon in which the balloon is separable at a required portion. However, this balloon catheter has the following problems:

Since the balloon has a complicated structure, it cannot be rendered small.

Further after the balloon has been expanded by accident, it cannot be contracted again.

Still further, it is feared that since the balloon is fitted only to the distal portion of the catheter, it may fall off by accident during its operation.

A similar balloon catheter is disclosed in the Japanese unexamined patent application publication Sho 59-34269. Since the balloon is also only fitted to a cannula, it may fall off by accident. If the connecting strength of the fitting portion is enhanced, the balloon can be prevented from falling off. However, it becomes difficult to separate the balloon from the catheter; the balloon gives an excess stress to the blood vessel to be occluded; and such a bulky structure of the balloon may cause the breakage thereof.

The balloon can be threadably connected to the catheter by means of screw. When the balloon is to be separated from the distal portion of the catheter assembly, however, the torque is not easily transmitted to the connecting portion of the balloon with the result that this may cause such trouble that the balloon would not be easily separated from the catheter, and the balloon would be twisted to be broken as well.

As a method of introducing an occluding balloon to a dwelling portion of blood vessel, such as a peripheral blood vessel e.g. a cerebral blood vessel, the balloon is slightly expanded in advance to be carried by a blood stream. However, this method is not suitable for sending an occluding balloon to a vascular portion where a blood flow is rather weak. This method is not applicable to the transmission of the balloon to the vicinity of a heart.

The method of transmitting an occluding balloon in a blood vessel while exposing the balloon as disclosed in the PCT Patent Publication Sho 57-500720, will not only lead to the breakage of the balloon but makes it difficult to easily and accurately transmit the balloon to the required dwelling portion.

This invention provides a balloon catheter assembly in which a balloon does not easily fall off during the transmitting operation thereby ensuring the introduction of the balloon to the required portion to be occluded, and, even if the balloon is expanded by accident, it can be contracted to the original size if a filler has not yet been gelled.

This invention further provides a balloon catheter assembly in which an operator can easily observe how a balloon occludes the required portion.

The invention still further provides a balloon catheter which is simple in structure and in which a balloon can be rendered small and can not be easily broken.

SUMMARY OF THE INVENTION

This invention is fundamentally characterized by comprising an expandable balloon having an opening at a proximal portion thereof, an inner tube having a distal portion detachably fitted in the opening of the balloon, a chuck surrounding a distal portion of the inner tube and fixed to an outer peripheral surface the inner tube, the chuck having a plurality of holding pieces whose distal ends extend outwardly and radially, and an outer tube coaxially surrounding the inner tube leaving a space therebetween, wherein the holding portions are adapted to be pressed inwardly by a distal end of the outer tube to hold the proximal portion of the balloon when the inner tube is pulled into the outer tube, and the holding portions are automatically opened and expanded to release the proximal portion of the balloon when the chuck is pushed out of the distal end of the outer tube.

With the catheter assembly having the fundamental structure as described above, a check valve may be provided at the proximal end of the outer tube such that the inner tube is extended out through the check valve thereby preventing a body fluid such as blood from flowing reversely when the distal portion of the catheter is inserted into a body.

Further, an infusion port may be connected to the check valve provided at the outer tube, and another infusion port for a balloon expanding filler may be connected to the proximal end of the outer tube.

Still further, the unexpanded balloon may be properly accommodated in the distal portion of the outer tube.

This invention is characterized by having a further fundamental structure comprising an expandable balloon having an opening at a proximal portion thereof, an inner tube having a distal portion detachably inserted in the opening of the balloon, an intermediate tube coaxially surrounding the inner tube leaving a space therebetween and provided at a distal portion thereof with a chuck having a plurality of openable holding pieces, and an outer tube coaxially surrounding the intermediate tube leaving a space therebetween, wherein the chuck is pulled in the outer tube, and the chuck releases the proximal portion of the balloon when the chuck is pushed out of the distal end of the outer tube.

With the catheter assembly having the second fundamental structure, the intermediate and outer tubes may have connectors connected to respective check valves provided at the proximal ends of the intermediate and outer tubes such that the intermediate tube is extended outwardly through the check valve of the outer tube and the inner tube is extended outwardly through the check valve of the intermediate tube thereby preventing a body fluid such as blood from flowing reversely.

Further, infusion ports may be connected to the check valves at the inner and outer tubes, and another infusion port for a balloon expanding filler may be connected to the proximal end of the inner tube.

Still further, the unexpanded balloon may be suitably installed in the distal end of the outer tube.

More further, a circular thick portion is formed at the middle circular portion of the balloon such that the balloon takes a bottle-gourd shape when it is expanded.

This invention further provides a balloon catheter assembly which comprises a balloon catheter in which a balloon communicates with the distal end of a multitube unit comprising an inner tube and an outer tube slidably and coaxially mounted thereon, and a chuck which selectively opens and closes at the distal end of the outer tube selectively to hold and release the balloon, a guide sheath which has a tube body having such an inner diameter that the guide sheath permits the balloon catheter to be guided and which guides the balloon to a required dwelling portion, and a guide sheath which guides the balloon to a required dwelling portion.

It is preferred that a check valve be connected to the proximal end of the guide sheath and an infusion port in series.

It is also preferred that the guide sheath is made of material mixed with X-ray opaque substance.

BRIEF DESCRIPTION OF DRAWINGS

FIGS. 6 and 7 are cross-sectional views of other embodiments of the occluding balloon catheter assembly according to this invention;

FIG. 8 is a perspective view of the inner tube of the catheter in FIG. 7;

FIGS. 11 to 13 are cross-sectional views of modifications of the balloon.

DETAILED DESCRIPTION

Figure 1:
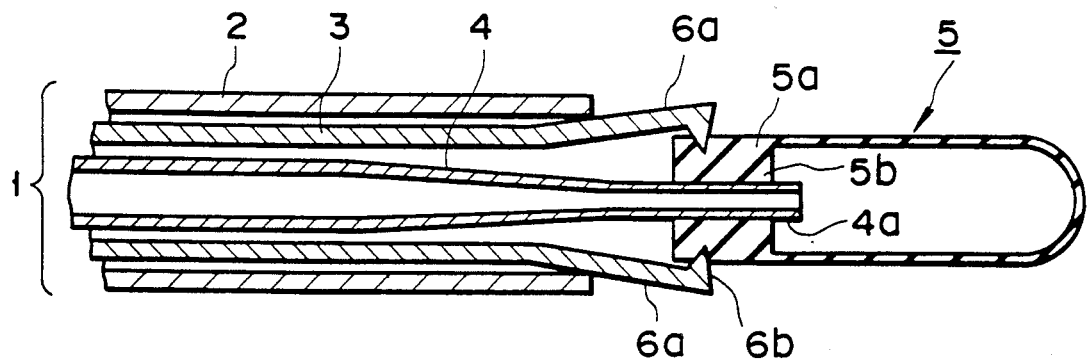
FIG. 1 is an enlarged cross-sectional view of the distal portion of a occluding balloon catheter according to this invention.

This invention will be explained with reference to embodiments shown in the drawings.

FIG. 1 shows the distal portion of the occluding balloon catheter according to this invention. As seen from this figure, a main catheter 1 is formed with a triple-tube unit comprising an outer tube 2, an intermediate tube 3 and an inner tube 4 arranged coaxially with each other. The inner tube 4 has a slightly thinner distal portion 4a and is inserted in an opening 5b formed in the center of the proximal portion 5a of a balloon 5 so as to communicate with the interior of the balloon 5.

Figure 2:
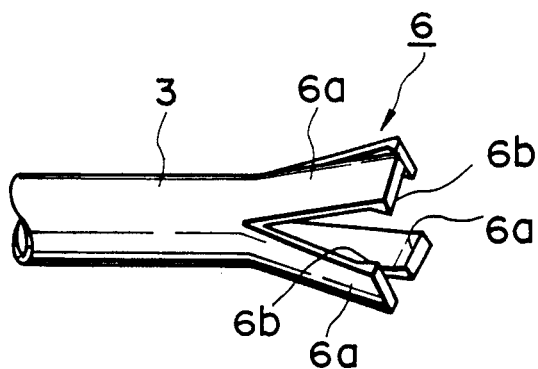
FIG. 2 is a perspective view of an intermediate tube of the catheter in FIG. 1.

The intermediate tube 3 surrounding the inner tube 4 at a spacing is formed at its distal end with a chuck portion 6 having a plurality of holding portions 6a which selectively opens and closes. As shown in FIG. 2, the holding portions 6a forming the chuck portion 6 are four in number and are integral with the intermediate tube 3. They normally open most widely at their distal ends, and the inner diameter defined by their distal ends is much larger than the outer diameter of the proximal portion 5a of the balloon when they are opened. On the distal end of each of the holding portions 6a is formed a hook 6b projecting inwardly of the chuck 6. The hooks 6b bite into the outer peripheral wall of the proximal portion 5a of the balloon 5 to hold the same, at the time of engagement as shown in FIG. 1.

The outer tube 2 surrounding the intermediate pipe at a spacing from the outer periphery of the outer tube 2 has at its distal end an inner diameter much smaller than the diameter defined by the distal end of the chuck 6 formed on the intermediate tube 3 when the chuck is expanded such that the movement of the intermediate tube 3 into and out of the outer tube 2 causes the chuck 6 to be pushed inwardly by the intermediate tube 3 and to be released therefrom, respectively, whereby the chuck 6 freely closes or opens.

Figure 3:
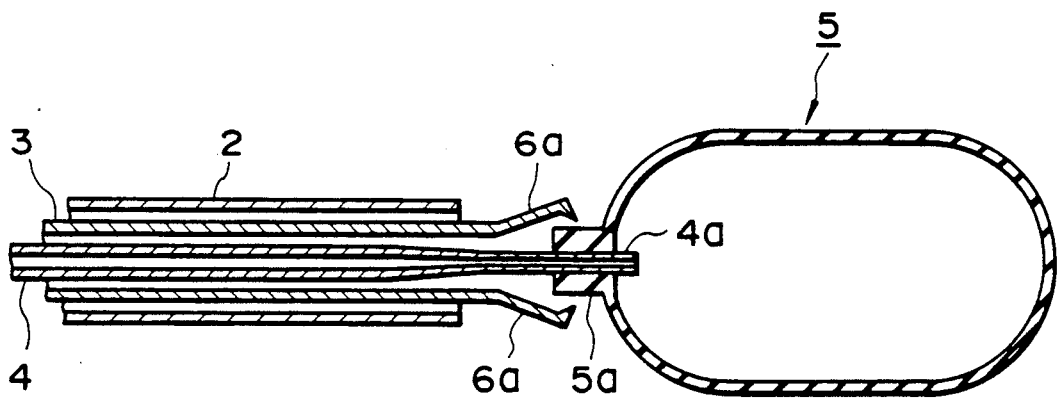
FIG. 3 is a cross-sectional view of the same embodiment as that in FIG. 1, with the balloon expanded.

When a filler is introduced into the balloon 5 through the inner tube 4, the balloon 5 is expanded as shown in FIG. 3. The material of the balloon 5 may be mixed with X-ray opaque substance such as platinum, gold or the like which constitutes a marker.

The total structure of this occluding catheter assembly will be explained.

Figure 4:
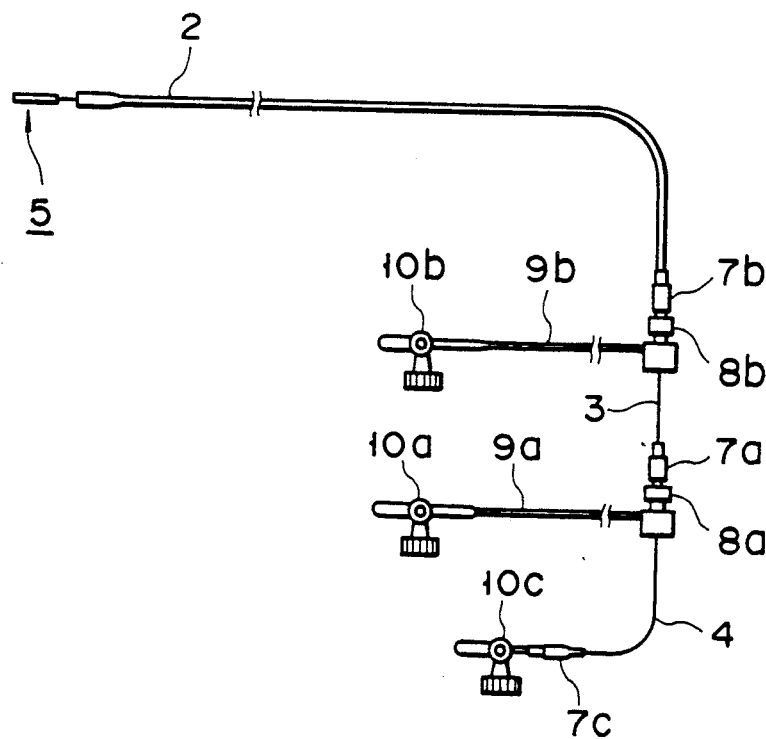
FIG. 4 is a plan view of an embodiment of the overall occluding balloon catheter assembly according to this invention.

As shown in FIG. 4, the proximal ends of the intermediate tube 3 and the outer tube 2 are connected to check valves 8a and 8b, respectively, via connectors 7a and 7b. However, the connectors 7a and 7b are not always necessary, but the proximal ends of the intermediate tube 3 and the outer tube 2 may be directly connected to the respective check valves 8a and 8b. Further, the intermediate tube 3 is led out from the outer tube 2 through the check valve 8b connected to the outer tube 2, and likewise the inner tube 4 is led out from the intermediate tube 3 through the check valve 8a connected to the intermediate tube 3, thereby preventing a body fluid such as blood from flowing reversely.

As shown in FIG. 4, the check valves 8a and 8b are connected to infusion ports 10a and 10b comprising two-way valves, three way valves or the like, respectively, via connecting tubes 9a and 9b. Physiological salt solution, for example, is infused continuously of intermittently in the tubes 3 and 4 through the infusion ports 10a and 10b, so that blood or other body fluid which would otherwise enter the outer tube 2 and the intermediate tube 3 during the operation of the catheter, is excluded. This process is intended to prevent blood or the like entering the catheter from being coagulated so as to operate the catheter normally.

An infusion port 10c (preferably, a two-way valve or a three-way valve) is connected to the proximal end of the inner tube 4 via a connector 7c so as to infuse a balloon expanding filler.

In general, the inner tube 4, the intermediate tube 3 and the outer tube 2 are made of such thermoplastic resin as polyethylene, polyolefin, ethylene-vinylacetate copolymer, polyester, polyvinylchloride, polyurethane, fluoric resin and nylon.

The material of the balloon 5 can be selected form elastic material such as silicone rubber, polyurethane and latex. A mesh made of nylon, polyethelene terephthalate, polyurethane or the like is embedded in the thick portion of the balloon 5 such that the balloon 5 is not expanded beyond a required size.

Figure 5:
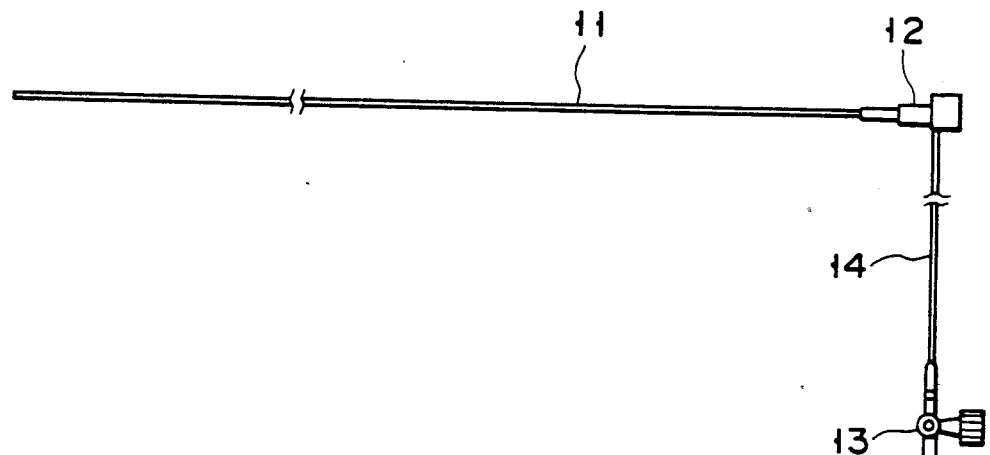
FIG. 5 is a plan view of an embodiment of the guide sheath.

A guide sheath 11 comprises a tube body having an inner diameter permitting the catheter 1 as well as the balloon 5 to be inserted into the sheath 11. As shown in FIG. 5, a connector 12 accommodating a check valve is preferably connected to the proximal end of the guide sheath 11. An infusion port 13 for infusing physiological salt solution into the guide sheath 11 connected to the connector 12 via a tube 14. This arrangement hinders the reverse flow of blood or the like when the guide sheath 11 is inserted in the body and excludes the blood or the like which has entered the guide sheath 11 by means of physiological salt solution or the like.

Like the catheter 1, the guide sheath 11 is generally made of thermoplastic resin such as polyolefin, ethylene-vinylacetate copolymer, polyester, polyvinylchloride, polyurethane, fluoric resin or nylon.

There will be explained the process how to dwell the balloon in a blood vessel by using the balloon catheter assembly.

First, a guide wire (not shown) is moved to a balloon dwelling portion by the similar method of angiography. The guide wire may be further advanced beyond the dwelling portion. Secondly, the guide sheath 11 set with a dilator (not shown) is inserted into the blood vessel along the guide wire until it reaches the balloon dwelling portion. The dilator is required when the guide sheath 11 begins to be inserted into the blood vessel, but it may be removed when the guide sheath 11 is moved to the balloon dwelling portion. Thirdly, the guide wire is removed when the guide sheath 11 has been moved to the balloon dwelling portion.

Thereafter, the catheter 1 is introduced to the dwelling portion through the guide sheath 11 with the balloon 5 held at the distal end of the catheter 1 as shown in FIG. 1. During the introduction of the catheter 1, the balloon 5 does not fall off because its distal portion 5a is firmly held by the chuck 6 formed on the distal end of the intermediate tube 3.

After the balloon 5 has been positioned in the dwelling portion as described above, the balloon expanding filler is introduced in the balloon 5 through the infusion port 10c at the proximal end of the inner tube 4 to expand the balloon 5 to a required size as shown in FIG. 3. The filler is made of gelable liquid such silicone RTV (Silicone Rubber KE12 RTV —a trade name of Shin-etsu Kagaku Kogyo Kabushiki Kaisha), cross-linked type modified polyvinyl alcohol or the like (with which X-ray opaque substance such as tungsten, bismuth oxide, barium sulfate or the like may be mixed). When the filler is mixed with the X-ray opaque substance, the catheter assembly can be used in X-ray fluoroscopy.

After the filler has been cured in the balloon 5, the outer tube 2 is retracted towards the proximal ends of the intermediate tube 3 and the inner tube 4, whereby the check 6 opens automatically and is disengaged from the proximal portion 5a of the balloon 5. Then, the distal end of the inner tube 4 is released from the proximal portion 5a of the balloon 5 by pulling the inner tube 4 towards it proximal end with the balloon 5 left in the required dwelling portion. If necessary, physiological salt solution is continuously or intermittently infused into the catheter through the infusion ports 10a and 10b.

In the above embodiment, the outer tube 2 has the same diameter over its entire length. As shown in FIG. 6, however, the distal portion 2a may be expanded to have such a large inner diameter that the portion 2a admits the unexpanded balloon 5 with the proximal portion 5a of the balloon 5 held by the chuck 6 formed on the intermediate tube 3. This structure is preferably used to hinder the balloon 5 from being damaged while the balloon 5 is being moved to the dwelling portion.

In FIG. 7 is shown another embodiment of the distal portion of the occluding balloon catheter according to this invention. As clearly understood from this figure, a catheter 21 has a double-tube unit comprising an outer tube 22 and an inner tube 23 coaxial therewith. The distal portion 23a of the inner tube 23 is formed slightly thinner than its remaining part and is inserted in an central opening 24b formed in the center of the proximal portion 24a of a balloon 24 so as to communicate with its interior.

On the distal end of the inner tube 23 is formed a chuck 25 comprising three holding pieces 25a arranged equidistantly in the circumferential direction so as to surround the distal portion 23a of the inner tube 23. As shown in FIG. 8, the holding portions 25a or normally opened most widely at their distal ends in such a manner that they can hold the outer peripheral surface of the proximal portion 24a of the balloon 24.

The distal end of each of the holding pieces 25a is formed with an inwardly projecting hook 25b. The hooks 25b bite in the outer peripheral surface of the proximal portion 24a of the balloon 24 to hold the same when the balloon 24 is connected to the catheter 21 as shown in FIG. 7.

The distal portion of the outer tube 22, which surrounds the inner tube 23 at a spacing from its outer peripheral surface, has an inner diameter much smaller than the diameter of the distal end of the chuck 25 formed on the inner tube 23 when the chuck 25 is opened. The movement of the inner tube 23 into and out of the outer tube 22 causes the chuck 25 to be pushed inwardly by the outer tube 22 and released therefrom, respectively, whereby the chuck 25 freely closes or opens.

Figure 9:
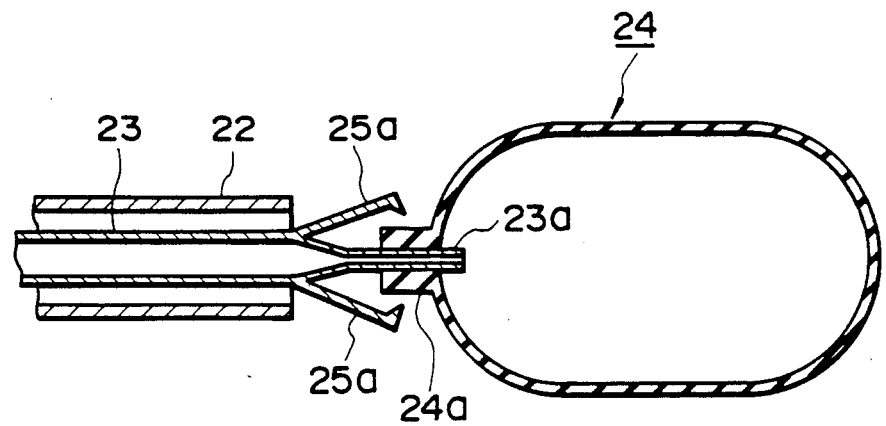
FIG. 9 is a cross-sectional view of the same embodiment as that in FIG. 7, with the balloon expanded.

The structure, functions and usage of this embodiment other than those as described above are the same as those of the embodiment shown in FIG. 1. As shown in FIG. 9, after the balloon 24 has been expanded to a required size, the outer tube 22 is moved towards the proximal end of the inner tube 23 to open the chuck 25a, and then the inner tube 23 is also pulled towards it proximal end, whereby the distal portion 23a of the inner tube 23 is released from the proximal portion 24 of the balloon 24 with only the balloon 24 left in the required dwelling portion.

Figure 10:
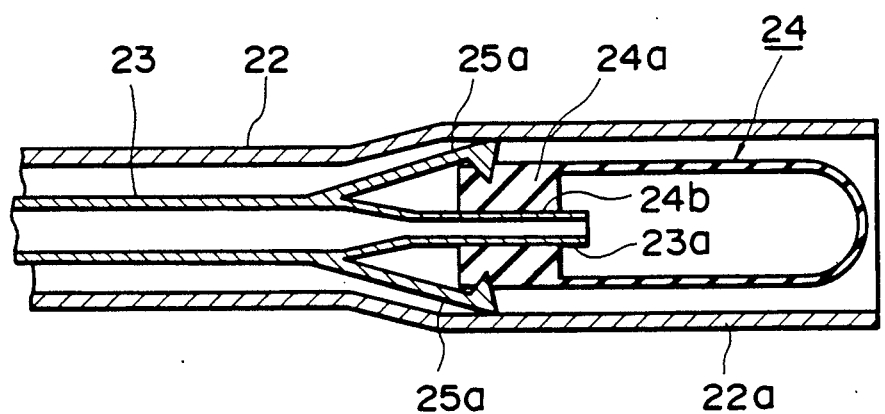
FIG. 10 is a cross-sectional view of another embodiment of the occluding balloon catheter.

This embodiment can be modified as shown in FIG. 10, in which the distal portion 22a may be expanded to have such a large diameter than the portion 22a admits the unexpanded balloon 24 with the proximal portion 24a of the balloon 24 held by the chuck 25 formed on the inner tube 22. This structure is preferably used to hinder the balloon 24 from being damaged while the balloon 24 is being moved to the dwelling portion.

The shape of the balloon is not limited to that of the balloon 24 of the second embodiment, but, as shown in FIG. 11, the distal portion 24c of the balloon 24 may be made solid, and a belt-type marker 24d made of X-ray opaque substance as described above may be fixed to or embedded in the outer peripheral surface of the portion 24c. Further, as shown in FIG. 12, the intermediate portion of the part, to be expanded, of the balloon 24 may be formed with a thick portion 24e so as to take a bottle-gourd shape when the balloon 24 is expanded as shown in FIG. 13. It is preferred that the opening 24b of the balloon 24 should be closed except when the inner tube is inserted in a blood vessel or the like such that the filler in the balloon is prevented from being discharged from the opening 24b.

The balloon catheter assembly according to this invention has such a structure that the catheter comprises a double-tube unit or a triple-tube unit in which the inner tube or the outer tube of the structures is provided at the distal end thereof with a freely openable and closable chuck thereby to hold or release the balloon. Therefore, the catheter assembly according to this invention provides the following technical features:

The balloon does not fall out during the operation of the catheter assembly and it becomes easy to collect the balloon again.

Further, when the balloon is expanded by accident, it can be contracted if the filler has not yet been gelled therein.

Still further, the breakage of the balloon can be prevented by installing the balloon in the outer tube.

In addition, the simple structure of the balloon enables the whole catheter assembly to be small-sized.

INDUSTRIAL APPLICABILITY

The balloon catheter assembly according to this invention is useful to occlude a blood vessel such as a patient's artery during percutaneous surgery.

We claim:

1. A balloon catheter assembly, comprising:
    an expandable balloon having an opening in a proximal end portion thereof and including a marker made of an X-ray opaque substance;
    an inner tube having a distal end portion which is removably inserted in said opening of said balloon;
    an intermediate tube coaxially surrounding said inner tube with a space therebetween;
    a chuck at a distal end of said intermediate tube, said chuck comprising a plurality of expandable and contractible holding portions; and
    an outer tube surrounding said intermediate tube with a space therebetween;
    said chuck being closed when pulled into said outer tube and pressed by said distal end of said outer tube to thereby hold said proximal end portion of said balloon, and said chuck being opened when pushed out of said distal end of said outer tube, to thereby release said proximal end portion of said balloon.

2. The balloon catheter assembly according to claim 1, wherein:
    said intermediate tube and said outer tube have proximal ends connected to respective check valves;
    said intermediate tube extends outward from said outer tube via said check valve connected to said outer tube; and
    said inner tube extends outward from said intermediate tube via said check valve connected to said intermediate tube, such that a body fluid is prevented from flowing reversely when said distal portion of said catheter is inserted in a body.

3. The balloon catheter assembly according to claim 2, further comprising infusion ports connected to said check valves which are connected to said intermediate tube and said outer tube, respectively.

4. The balloon catheter assembly according to claim 1, characterized in that said inner tube has a proximal end connected to a balloon expanding infusion port.

5. The balloon catheter assembly according to claim 1, wherein said inner tube, said intermediate tube and said outer tube are molded from a resin selected from the group consisting of polyethylene, polypropylene, ethylene-vinylacetate copolymer, polyester, polyvinylchloride, polyurethane, fluoric resin and polyamide.

6. The balloon catheter assembly according to claim 1, further comprising a balloon expanding filler made of material which assumes a liquid state when said filler is infused into said balloon and a gelled state at a predetermined time after said filler has been infused into said balloon.

7. The balloon catheter assembly according to claim 6, wherein said filler is mixed with an X-ray opaque substance.

8. The balloon catheter assembly according to claim 1, wherein said balloon is molded from at least one material selected from the group consisting of silicone rubber, polyurethane and latex.

9. The balloon catheter assembly according to claim 1, wherein said balloon has a circular middle portion which is thick such that said balloon takes a bottle-gourd shape when expanded.

10. The balloon catheter assembly according to claim 8, wherein said balloon includes a mesh molded from at least one material selected from the group consisting of nylon, polyethylene terephthalate and polyurethane, said mesh being buried therein so as to restrict the expansion degree of said balloon.

11. A balloon catheter assembly comprising:
    an expandable balloon having an opening in a proximal end portion, said proximal end portion having an outer peripheral surface;
    an inner tube having a distal portion removably inserted in said opening of said balloon;
    a chuck at said distal portion of said inner tube, said chuck surrounding said distal portion of said inner tube, and said chuck having a plurality of holding portions extending radially outwardly at distal ends thereof; and
    an outer tube coaxially surrounding said inner tube with a space therebetween, said outer tube having a distal end, said chuck being adapted to be closed when said inner tube is pulled in said outer tube by pushing said holding portions inwardly by said distal end of said outer tube to hold said proximal portion of said balloon on said outer peripheral surface thereof, and adapted to release said proximal portion of said balloon when projected from said distal end of said outer tube to be disengaged therefrom.

12. The balloon catheter assembly according to claim 11, wherein:
    said outer tube has a proximal end connected to a check valve; and
    said inner tube extends outward from said outer tube through said check valve, such that a body fluid is prevented from flowing reversely when said distal portion of said catheter is inserted in a body.

13. The balloon catheter assembly according to claim 11 further comprising an infusion portion connected to said outer tube.

14. The balloon catheter assembly according to claim 11, wherein said inner tube has a proximal end connected to an infusion port for injecting into said balloon a filler for expanding said balloon.

15. The balloon catheter assembly according to claim 11, wherein said inner tube and said are molded from a resin selected from the group consisting of polyethylene, polypropylene, ethylene-vinyl acetate copolymer, polyester, polyvinylchloride, fluoric resin and polyamide.

16. The balloon catheter assembly according to claim 11, further comprising a balloon expanding filler made of material which assumes a liquid state when said filler is infused into said balloon and a gelled state at a predetermined time after said filler has been fused into said balloon.

17. The balloon catheter assembly according to claim 11, wherein said filler is mixed with an X-ray opaque substance.

18. The Balloon catheter assembly according to claim 11, wherein said balloon is molded from at least one material selected from the group consisting of silicone rubber, polyurethane and latex.

19. The balloon catheter assembly according to claim 11, wherein said balloon has a circular middle portion which is thick such that said balloon takes a bottle-gourd shape when expanded.

20. The balloon catheter assembly according to claim 18, wherein said circular middle portion of said balloon includes a mesh molded from at least one material selected from the group consisting of nylon, polyethylene terephthalate and polyurethane, said mesh being buried therein so as to restrict the expansion degree of said balloon.

21. The balloon catheter assembly according to claim 18 wherein said balloon includes a marker made of X-ray opaque substance.

22. The balloon catheter assembly, comprising:
a balloon;
a balloon catheter including a multi-tube unit comprising an inner tube, an outer tube coaxial with said inner tube, and a chuck for selectively holding and releasing said balloon, said multi-tube unit having a distal end portion communicating with said balloon, said outer tube having a distal end at which said chuck is selectively opened and closed; and
a guide sheath comprising a tube body having such an inner diameter that said guide sheath admits said balloon catheter so as to introduce said balloon to a required dwelling portion.

23. The balloon catheter assembly according to claim 22, wherein said guide sheath has a proximal end connected to a check valve.

24. The balloon catheter assembly according to claim 23, further comprising an infusion port connected to said check valve.

25. The balloon catheter assembly according to claim 22, wherein said guide sheath is made of material mixed with an X-ray opaque substance.

26. The balloon catheter assembly according to claim 1, wherein said balloon includes a mesh molded from at least one material selected from the group consisting of nylon, polyethylene terephthalate and polyurethane, said mesh being buried therein so as to restrict the expansion degree of said balloon.

27. A balloon catheter assembly, comprising:
an expandable balloon having an opening in a proximal end portion thereof;
an inner tube having a distal end portion which is removably inserted in said opening of said balloon;
an intermediate tube coaxially surrounding said inner tube with a space therebetween;
a chuck at a distal end of said intermediate tube, said chuck comprising a plurality of expandable and contractible holding portions; and
an outer tube surrounding said intermediate tube with a space therebetween;
said chuck being closed when pulled into said outer tube and pressed by said distal end of said outer tube to thereby hold said proximal end portion of said balloon, and said chuck being opened when pushed out of said distal end of said outer tube, to thereby releases said proximal end portion of said balloon; and wherein
said intermediate tube and said outer tube have proximal ends connected to respective check valves;
said intermediate tube extends outward from said outer tube via said check valve connected to said outer tube; and
said inner tube extends outward from said intermediate tube via said check valve connected to said intermediate tube, such that a body fluid is prevented from flowing reversely when said distal portion of said catheter is inserted in a body.

28. The balloon catheter assembly according to claim 27, further comprising infusion ports connected to said check valves which are connected to said intermediate tube and said outer tube, respectively.

29. A balloon catheter assembly, comprising:
an expandable balloon having an opening in a proximal end portion thereof;
an inner tube having a distal end portion which is removably inserted in said opening of said balloon;
an intermediate tube coaxially surrounding said inner tube with a space therebetween;
a chuck at a distal end of said intermediate tube, said chuck comprising a plurality of expandable and contractible holding portions; and
an outer tube surrounding said intermediate tube with a space therebetween;
said chuck being closed when pulled into said outer tube and pressed by said distal end of said outer tube to thereby hold said proximal end portion of said balloon, and said chuck being opened when pushed out of said distal end of said outer tube, to thereby release said proximal end portion of said balloon; and
wherein said balloon has a circular middle portion which is thick such that said balloon takes a bottle-gourd shape when expanded.

30. A balloon catheter assembly, comprising:
an expandable balloon having an opening in a proximal end portion thereof;
an inner tube having a distal end portion which is removably inserted in said opening of said balloon;
an intermediate tube coaxially surrounding said inner tube with a space therebetween;
a chuck at a distal end of said intermediate tube, said chuck comprising a plurality of expandable and contractible holding portions; and
an outer tube surrounding said intermediate tube with a space therebetween;
said chuck being closed when pulled into said outer tube and pressed by said distal end of said outer tube to thereby hold said proximal end portion of said balloon, and said chuck being opened when pushed out of said distal end of said outer tube, to thereby release said proximal end portion of said balloon;
said balloon being molded from at least one material selected from the group consisting of silicone rubber, polyurethane and latex; and
said balloon including a mesh molded from at least one material selected from the group consisting of nylon, polyethelene terephthalate and polyurethane, said mesh being buried therein so as to restrict the expansion degree of said balloon.

* * * * *